United States Patent [19]

Kataoka et al.

[11] Patent Number: 4,468,198
[45] Date of Patent: Aug. 28, 1984

[54] MANDIBULAR MOTION REPRODUCING DEVICE

[75] Inventors: Kenzo Kataoka, Otsu; Kazunari Matoba, Nara; Shinichi Osada, Kyoto, all of Japan

[73] Assignee: Kabushiki Kaisha Morita Seisakusho, Kyoto, Japan

[21] Appl. No.: 482,639

[22] Filed: Apr. 6, 1983

[30] Foreign Application Priority Data

Apr. 19, 1982 [JP] Japan .................................. 57-65631

[51] Int. Cl.³ .............................................. A61C 11/00
[52] U.S. Cl. ........................................ 433/63; 433/54; 433/64; 433/65
[58] Field of Search ......................... 433/54, 55, 56, 57, 433/58, 59, 61, 62, 63, 64, 65, 66, 67, 68, 69, 27, 73

[56] References Cited

U.S. PATENT DOCUMENTS

| 198,853 | 1/1878 | Oehlecker | 433/57 |
| 3,390,459 | 7/1968 | Seidenberg | 433/69 |
| 4,265,620 | 5/1981 | Moro et al. | 433/69 |
| 4,330,276 | 5/1982 | Becker et al. | 433/69 |
| 4,354,836 | 10/1982 | Santoni | 433/73 |

Primary Examiner—John J. Wilson
Attorney, Agent, or Firm—Koda and Androlia

[57] ABSTRACT

A mandibular motion reproducing device wherein a mandibular model supporting plate on which a mandibular model is fixed is deemed as a rigid plane, three points contained in this rigid plane are selected and marked, three reference points for reproduction are set each corresponding to one of the marked points and in a predetermined dimensional relationship therewith, drive means capable of shifting the individual reference points for reproduction along the coordinate axes of X, Y, Z respectively are connected therewith, the drive means have six alternative driving directions including the orthogonal X, Y and Z directions and are individually driven by inputting position coordinate information obtained from a measuring system and the resulting motions of the reference points for reproduction are synthesized for causing the rigid plate constituting the mandibular model supporting plate to undergo three-dimensional motion.

4 Claims, 5 Drawing Figures

MANDIBULAR MOTION REPRODUCING DEVICE

BACKGROUND OF THE INVENTION

1. Field of the Invention

The present invention relates to a mandibular motion reproducing device for enabling reproduction of the human mandibular motion with high precision by the use of a mating mandibular model and maxillary model.

2. Prior Art

It is, needless to say, quite important to have accurate knowledge and information about mandibular motion for proper execution of dental diagnoses, treatments and restorative operations such as the manufacture of prostheses used for restoration of the gnathic function, diagnosis of irregular occlusion, quantitative measurement of the amount of irregularity of occulusion or of the relationship between gnatho-articular defect and occlusion. Although recently it has become possible to obtain precise information about individual patients' gnathic motions thanks to the improved possibility of applying modern knowledges of optics, magnetics and electronics to the measurement of mandibular motion, such attempts have so far been limited to the gathering of information required for operation of articulator and diagnosis of gnathic motion. To date no successful attempt has been made for high-precision reproduction of gnathic motion on the basis of the gathered data. Worse, since the prior art measuring systems have been invariably of the type in which the measuring members are set in the mouth cavity of the patient, they have had fatal defect of being unable to gather information about the conditions the range from closure of the mouth to the mouth-opening of 2–3 mm, which is known to be most important for restoration of occlusion.

SUMMARY OF THE INVENTION

The inventor, therefore, provided earlier a mandibular motion diagnostic device (copending Japanese Application No. 57,721/82) comprising a measuring unit using position detecting members for gathering information about the positions of three measuring points set outside the patient's mouth cavity for position measurement as well as measurement of the amount of displacement thereof on a unique position coordinate plane as coordinate information, which enables reproduction by a mandibular model of the human mandibular motion with high accuracy in its reproducing system according to the position coordinate information obtained. The present invention relates to the above-described reproducing device, which is preferably to be used in combination with the measuring system developed by the same inventors, but is also capable of reproducing the mandibular motion even when it is used in combination with some other measuring device.

The working principle of the reproducing device of the present invention consists in that a mandibular model supporting plate on which a mandibular model is fixed is deemed as a rigid plane, three points contained in this rigid plane are selected and marked, three reference points for reproduction are each set corresponding to one of the marked points and in a predetermined dimensional relationship therewith, drive means capable of shifting the individual reference points for reproduction along the coordinate axes of X, Y and Z respectively are connected therewith, the drive means as a whole has six alternative driving directions including the orthogonal X, Y and Z directions and are individually driven by inputting the position coordinate information obtained in the measuring system and the resulting motions of the reference points for reproduction are synthesized for causing the rigid plate constituting the mandibular model supporting plate to undergo three-dimensional motion.

In the preferred embodiment described below the above-mentioned three marked points consist of one point corresponding to the anterior section of the mandibular model and two points corresponding to the lateral sections thereof. With these three points defining an isosceles triangle, the reference points for reproduction are set at the centers of movement of freely rotatable and bendable spherical joints or self-aligning joints, pulse motors are used as driving means, two each of which are connected with each reference point for reproduction in the two-dimensional directions perpendicular to each other (six in all) so that each joint is not only positively driven two-dimensionally but also allowed to move freely passively also in a third dimensional direction by the aid of a bearing slidable in this direction, and to a pair of pulse motors provided for each reference point for reproduction of the two-dimensional position coordinate information is inputted for the rigid plate constituting the mandibular model to undergo three-dimendional motion through the synthesis of two-dimensional motion at each reference point for reproduction with respect to the maxillary model.

When the reproducing device of the present invention is used, the patient who has once had his or her gnathic structure measured by the dentist need not visit him anymore, and the dentist can have the patient's gnathic motion accurately reproduced on an articulator on the basis of the obtained data anytime and anywhere. Hence the present invention is highly useful for dental analyses, treatments as well as restorative operations.

BRIEF DESCRIPTION OF THE DRAWINGS

This and other objects and advantages and further description will now be discussed in connection with the drawings in which.

DETAILED DESCRIPTION OF THE PREFERRED EMBODIMENTS

Figure 1:
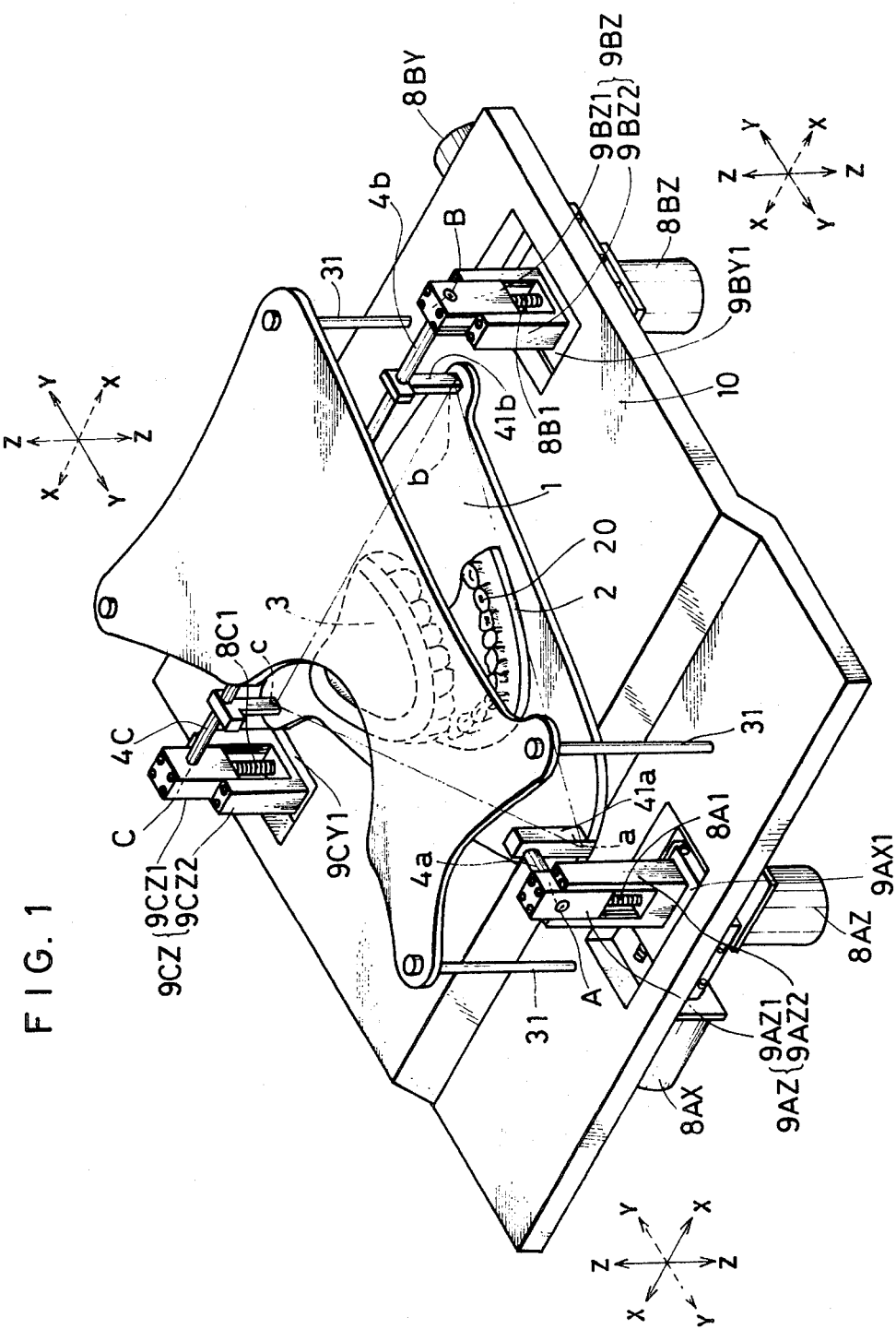
FIG. 1 is a perspective view of a reproducing device as an embodiment of the present invention.
Figure 2:
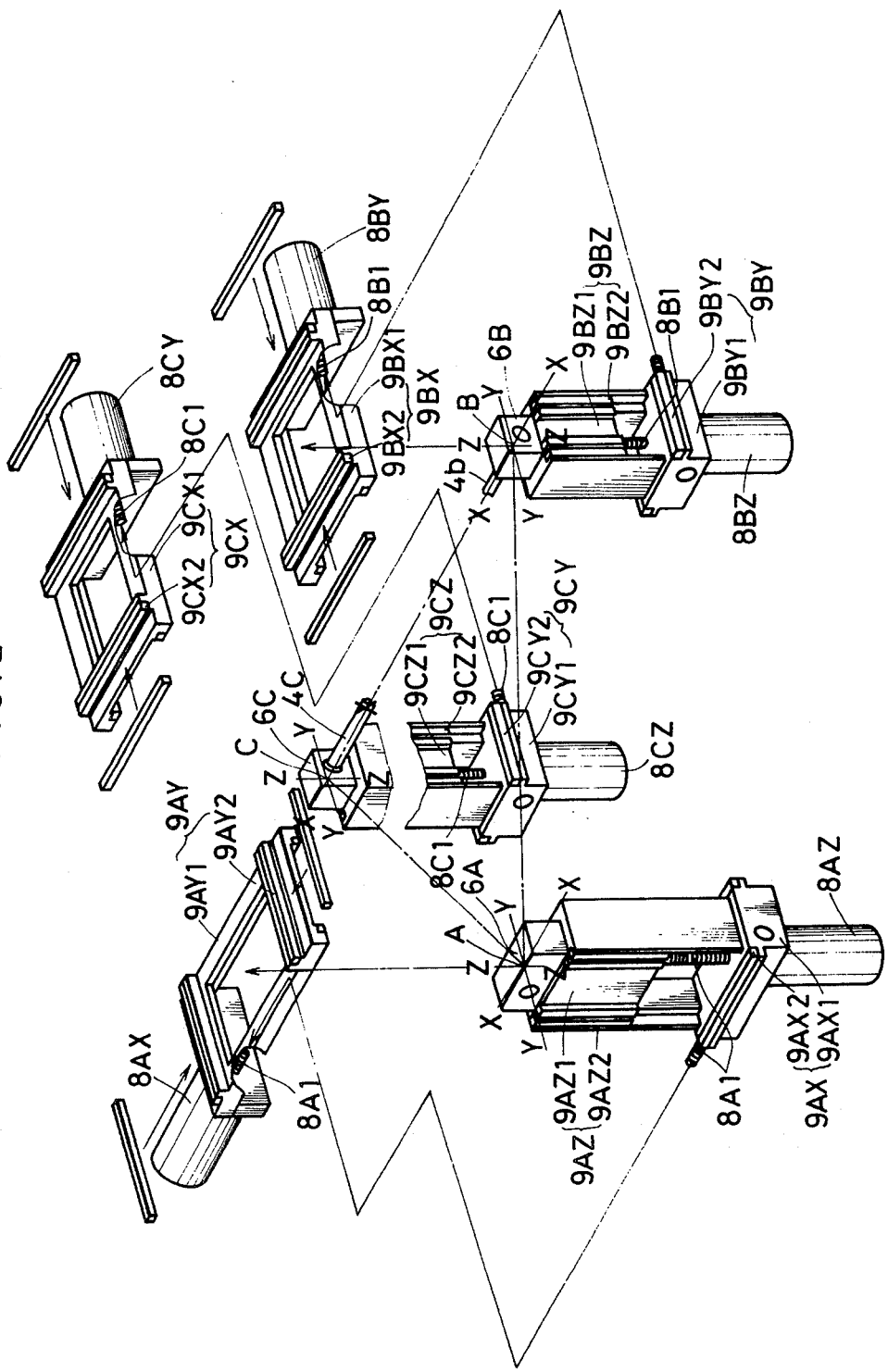
FIG. 2 is a schematic exploded view partly omitted showing the relationship between pulse motors and slide bearings in FIG. 1.

Referring to FIG. 1, numeral 1 designates a mandibular model supporting plate substantially of a single rigid plate, 2 is a mandibular model fixed on the supporting plate 1 representing a proper dental arch (to be described later), 3 is a maxillary model fixedly supported above the mandibular model 2 in an opposing relationship therewith by means of a base plate 10 and supporting legs 31, a, b, c are three marked points defining the rigid plane of the mandibular model supporting plate, in which a corresponds to the anterior section of the mandibular model 2 (more particularly the cutting edge opening of the anterior section) and b and c are two mutually symmetrical points in both posterior sections of the same model 2, and the isosceles triangle defined by the marked points a, b and c determines the above-described rigid plane. A, B, C are reference points for reproduction extending outwardly from the marked points a, b, c equidistant therefrom and outside the mandibular model supporting plate 1 by means of rigid rods 4a, 4b, 4c and set at the outer ends thereof, corresponding to the marked points a, b, c, 41a, 41b, 41c are fixed connectors whose positions are in fixed relationship with the corresponding parts 4a, 4b, 4c. For convenience in assembly 4b and 4c consist of a common rod, but these can be made of separate rods. In FIGS. 2 through 5, 5A, 5B and 5C are freely rotatable and bendable spherical joints or self-aligning joints and have set therein at the center of rotation (spherical center) thereof the ends of the rods 4a, 4b, 4c, i.e. the reference points for reproduction A, B, C. The spherical joints 5A, 5B, 5C are provided in holders 6A, 6B, 6C, respectfully, which are driven to slide by pulse motors 8AX, 8AZ, 8BY, 8BZ, 8CY, 8CZ disposed separately therefor in any two of the three orthogonal dimensional directions for a total of six driving directions including the orthogonal dimensional directions X, Y, Z, and each of the joints 5A, 5B, 5C is arranged to follow the sliding motion of the other two joints with regard to the remaining one dimensional direction. Concretely, the pulse motors 8AX and 8AZ are disposed in the X and Y directions, 8BY and 8BZ as well as 8CY and 8CZ are disposed in the Y and Z directions, and the joint 5A is arranged to follow others to slide in the remaining X direction and the joints 5B and 5C likewise provided in the remaining X direction respectively.

Figure 3:
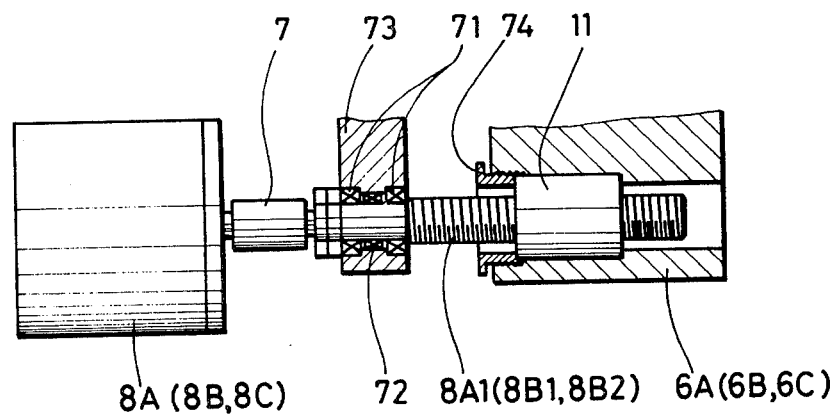
FIG. 3 is a vertical sectional side view showing the way a pulse motor is connected with a slide bearing.

For convenience in understanding, the driving direction of each pulse motor is indicated by the solid arrow and the direction in which each joint slides following the other joints driven positively in the same direction is indicated by the dotted arrow. In order to allow the joints 5A, 5B, 5C to make the above-described movements as they are driven by the motors 8A, 8B, 8C, the holders 6A, 6B, 6C are provided with three sliding guide means for sliding them in the orthogonal three directions with respect to the base plate 10, and concretely the joint 5A (box 6A) is composed of a slide bearing 9AX arranged to slide in the X direction, a slide joint 9AZ arranged to slide in the Z direction (these together compose a bearing slidable in two orthogonal directions) and a slide bearing arranged to slide in the Y direction following other joints driven in the same direction combined vertically one upon another. It will be apparent that when the pulse motors 8AX, 8AZ are driven, the spherical joint 5A is driven in the X and Y directions through the slide bearings 9AX, 9AZ and passively driven in the remaining Y direction through the slide bearing 9AY. Similarly, with the joints 5B, 5C, it will be understood that these are driven to slide in the Y and Z directions through the orthogonal slide bearing 9BY, 9BZ and 9CY, 9CZ and are passively driven to slide in the remaining X direction through the slide bearing 9BX, 9CX. Each of these slide bearings 9AX .. . etc. consists of a pair of sliding members and rail members also provided with a plurality of rollers linearly arranged between their sliding faces. For convenience in understanding, those belonging to the first category are distinguished by a suffix 1 and those belonging to the second category by a suffix 2, but those belonging to the third category are not shown in the figure. As to the pulse motors 8A, 8B, 8C and the holder 6A, 6B, 6C, it is shown in FIG. 3 that the motor 8A (8B and 8C are here omitted) has connected to its shaft a screw rod 8A1 finely male-threaded. In the holder 6A there is fixedly provided a nut 11 female-threaded to a mate with the rod 8A1 (not shown), and these are screwed together so that, when the pulse motor 8A rotates, the holder 6A is driven forward and backward with fine adjustment. This relationship is identical for the motors 8B, 8C and holders 6B, 6C, too.

Figure 4:
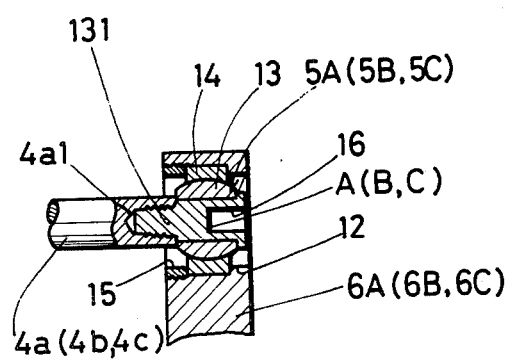
FIG. 4 is an enlarged vertical sectional side view showing the relationship between the slide bearing and a spherical joint.

In FIG. 3, 7 is a shaft joint connected to the motor shaft, 71 a thrust bearing, 72 a radial bearing, 73 a bearing connected to the base plate 10, and 74 a holding screw. The way the holder 6A (6B, 6C), rod 4a (4b, 4c) and spherical joint 5A (5B, 5C) are combined is illustrated in FIG. 4. A tapped hole 4a1 is made in one end of the rod 4a, into which a threaded rod portion 131 of a spherical body 13 of the spherical bearing 5A is screwed for connection of these two parts, and the connected unit is set in a mating bore 12 provided in the holder 6A to be carried by a spherical socket 14 held therein 12. On the opposite side, a retainer ring 15 is pushed into the bore 12 to prevent slipping out of the socket 14 in the direction of thrust. The center of this spherical body 13 is the above-described reference point for reproduction A (B, C). On one side of this spherical body 13, there is provided a hole 16 to accommodate a measuring rod (not shown) whose inward end face matches the reference point A. It is apparent that the above arrangement allows the rod 4a to be freely rotatable and bendable with respect to the holder 6A through the spherical joint 5A.

Figure 5:
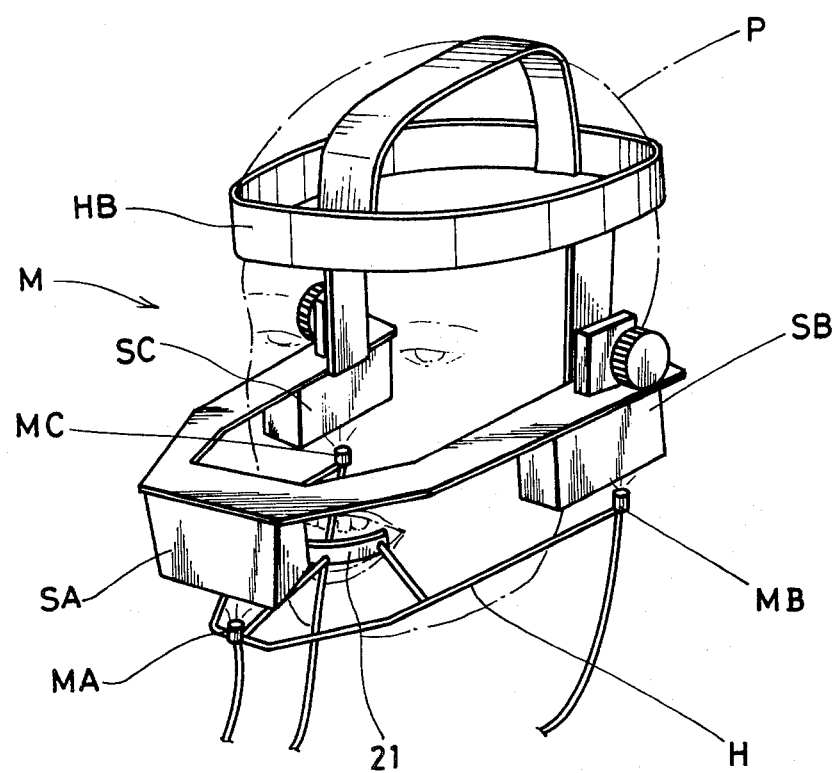
FIG. 5 is a schematic illustrative view of a measuring device preferred for use in combination with the reproducing device of the present invention.

By proper positional relationship for the dental arch 20 of the mandibular model is meant that the dental arch 20 of the mandibular model on the mandibular model supporting plate 1 is properly positioned with respect to the above-mentioned marked points a, b, c. In other words, it means, as seen from FIG. 5, that, when in a measuring device M for the mandibular motion of a patient p three measuring points MA, MB, MC set along the patient's mandible as points of motion with their relative positional relationship with respect to the patient's mandible kept constant as they are in motion properly correspond to the above-described marked points a, b, c, the patient'dental arch 21 and the dental arch 20 of the mandibular model 2 are in proper corresponding relationship with the mandibular model supporting plate 1. As to such positioning of the dental arch 20, recommended is reference to the specification of a co-pending patent application titled "Reference Rod in Mandibular Motion Diagnostic Device" filed by the present Applicant. Proper positioning of the dental arch 20 is a prerequisite for occlusal motion of the mandibular model with respect to the maxillary model accurately reproducing the patient's mandibular motion. Since, however, the present invention has as its important background the mechanism of causing the mandibular model to make three-dimensional motion, explanation about proper positioning of the dental arch 20 is herein omitted. In connection with the measuring device M, now given is an example of the position coordinate information to be inputted to the pulse motors 8A, 8B, 8C for control thereof. Referring to FIG. 5, in the measuring device M the measuring points Ma, Mb, Mc (actually spot light sources) corresponding to the marked points a, b, c are set as described above on the holding rod H to have their relative positions with respect to the patient p's maxilla constant throughout the measuring time. There are also provided three position detectors SA, SB, SC corresponding to the measuring points MA, MB, MC, the position information at the three measuring points MA, MB, MC being measured as two-dimensional position coordinate information at points of orthogonal projection onto the respective two-dimensional coordinate planes (not shown) of the position detectors SA, SB, SC, and the measured data is stored in the memory (not shown) after proper data-processing in the computing unit (not shown). Meanwhile, the three holders 6A, 6B, 6C move in the reference planes for reproduction (not shown) with their relative positions equal to those of the two-dimensional coordinate planes of the position detectors SA, SB, SC, and regardless of their positions in the planes, hold the rods 4a, 4b, 4c to be orthogonal to the respective planes so that the reference points for reproduction A, B, C in the spherical joints 5A, 5B, 5C can be orthogonally projected onto the above-described planes.

In the setup described above, when the amount of displacement as a function of time of the measuring points MA, MB, MC of the measuring device having been inputted to the respective pulse motors 8A, 8B, 8C from the above-described memory as position information indicating their coordinates in the two-dimensional coordinate plane, the pulse motors are started to drive the holders 6A, 6B, 6C to slide in the two-dimensional directions. Accordingly the spherical joints 5A, 5B, 5C are respectively caused to slide in the same directions through the rods 4a, 4b, 4c and follow the movement of other joints in the remaining one dimensional direction. Since the moving directions of the joints 5A, 5B, 5C as a whole include the orthogonal three dimensional directions, the reference points for reproduction A, B, C in the joints 5A, 5B, 5C are caused to have three-dimensional motion. Hence the isosceles triangular rigid plane defined by these reference points A, B, C, i.e. the mandibular model supporting plate 1, has three-dimensional motion to precisely reproduce the patient p's mandibular motion. In the above process, it is apparent that the joints 5A, 5B, 5C are caused to rotate and bend as the rods 4a, 4b, 4c are positively driven to slide and also follow the movement of others, and the above-described mandibular motion results from synthesis of the motions of the joints 5A, 5B, 5C.

Thus, in this preferred embodiment of the present invention the three-dimensional mandibular motion is detected and reduced to two-dimensional pieces of position information as function of time and the mandibular model supporting plate is caused to have a three-dimensional motion through position control of the three reference points for reproduction in a fixed positional relationship with the mandibular model supporting plate according to the two-dimensional position information thus obtained. Hence with it, the mechanisms for reproduction of complicated elements of motion or combinations thereof such as rotation of the mandibular model with respect to the maxilla model, rotation accompanied by shifting of the center axis of rotation, torsional motion about the center axis, and synthesis of rotation and torsional motion can be totally dispensed with, and high-precision reproduction of the mandibular motion can be accomplished through the combination of relatively simple mechanisms.

Although in the cited embodiment each reference point for reproduction was caused to make two-dimensional motion according to orthogonal two-dimensional information, it suffices if a total of six dimensional (driving) directions are involved including the orthogonal three dimensional directions X, Y, Z. Hence, for instance, it is also possible to arrange so that position control of one reference point for reproduction is made three-dimensionally, another two-dimensionally and a third one-dimensionally and the mandibular motion is reproduced through synthesis of these motions. Needless to say, other arrangements than in the cited preferred embodiment are feasible with regard to setting directions, number of slide bearings, the dimensional position coordinates of input information and so on.

We claim:

1. A mandibular motion reproducing device comprising:
   a mandibular model supporting plate substantially of a single rigid plate;
   a mandibular model fixed on said mandibular model supporting plate in proper positional relationship with regard to a dental arch;
   a maxilla model fixedly supported above said mandibular model in proper positional relationship with respect thereto;
   three marked points set on said mandibular model supporting plate;
   three reference points set for reproduction corresponding to said individual marked points set in a fixed positional relationship to said marked points;
   joint means for allowing free rotation and bending of said respective reference points for reproduction;
   sliding guide means for allowing free sliding of said respective joint means in any of orthogonal three dimensional directions X, Y, Z; and
   drive means for driving said respective joint means in any of said directions,
   wherein said drive means having a total of six possible driving directions including orthogonal three dimensional directions, said joint means having therein said reference points for reproduction at the center of motion thereof and each thereof follows the movement of other joint means in directions other than those in which it is being driven, and said drive means having inputted thereto position coordinate information obtained in a measuring system and cause said mandibular model to move three-dimensionally with respect to said maxillary model through position control of said individual joint means according to said position coordinate information.

2. A mandibular motion reproducing device as defined in claim 1, wherein one of said three marked points corresponds to the anterior section of said mandibular model and the other two thereof correspond to both lateral sections thereof and the isosceles triangle defined by said three marked points determines a rigid plane of said mandibular model supporting plate, said sliding guide means are bearing slidable in two of the orthogonal three dimensional directions X, Y, Z, said drive means are pulse motors with their driving directions corresponding to said two dimensional directions and said drive means have inputted thereto said two-dimensional position coordinate information and cause said mandibular model to move three-dimensionally through synthesis of said two-dimensional motions of said joint means.

3. A mandibular motion reproducing device as defined in claim 2, wherein said marked points are connected with said corresponding joint means by rigid rods, each of said orthogonal slide bearings is connected with a pair of pulse motors each including one corresonding joint means by means of screw rods to be freely movable forward and backward and the orthogonal slide bearing is linked with other slide bearings for its following slide motion in the remaining one dimensional direction.

4. A mandibular motion reproducing device as defined in claims 1 or 2, wherein said position coordinate information obtained in said measuring system is stored in memory means to be subsequently inputted to said respective drive means.

* * * * *